United States Patent
Reyes (10) Patent No.: US 10,663,468 B2
(45) Date of Patent: May 26, 2020

(54) HIGH THROUGHPUT METHODS FOR VIRUS QUANTIFICATION

(71) Applicant: BOEHRINGER INGELHEIM ANIMAL HEALTH USA INC., Duluth, GA (US)

(72) Inventor: Jean Reyes, Lyons (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 216 days.

(21) Appl. No.: 15/215,106

(22) Filed: Jul. 20, 2016

(65) Prior Publication Data

US 2017/0023570 A1  Jan. 26, 2017

Related U.S. Application Data

(60) Provisional application No. 62/196,886, filed on Jul. 24, 2015.

(51) Int. Cl.
*G01N 33/569* (2006.01)
*G01N 15/14* (2006.01)
*G01N 33/58* (2006.01)
*G01N 15/10* (2006.01)

(52) U.S. Cl.
CPC ... *G01N 33/56983* (2013.01); *G01N 15/1463* (2013.01); *G01N 33/582* (2013.01); *G01N 2015/1006* (2013.01); *G01N 2015/1486* (2013.01)

(58) Field of Classification Search
None
See application file for complete search history.

(56) References Cited

U.S. PATENT DOCUMENTS 6,248,514 B1  6/2001 Hutchins et al.
7,476,507 B2  1/2009 Allibert et al.

FOREIGN PATENT DOCUMENTS

WO  1998001582  1/1998
WO  WO 02/090550 A2 * 11/2002 ............... C12N 7/00

OTHER PUBLICATIONS

Payne et al. Quantitation of flaviviruses by fluorescent focus assay, J. Virol. Met. 2006; 134: 183-189.*
Fritschy and Härtig, "Immunofluorescence" in Encyclopedia of Life Sciences, 2001 John Wiley & Sons, Ltd downloaded from www.els.net.*
Shimizu et al. Evidence for in vitro replication of hepatitis C virus genome in a human T-cell line. Proc. Natl. Acad. Sci. USA, 1992; 89: 5477-5481.*
Li et al. Detection of Infectious Adenoviruses in Environmental Waters by Fluorescence-Activated Cell Sorting Assay, Appl. Environ. Microbiol.; 2010; 76(5): 1442-1448.*
H.M Shapiro, "The Evolution of Cytometers", Cytometry Part A; 2004; 58A:13-20.*

(Continued)

*Primary Examiner* — Janet L Andres
*Assistant Examiner* — Stuart W Snyder
(74) *Attorney, Agent, or Firm* — Judy Jarecki-Black; Steffan Finnegan (57) ABSTRACT

This invention relates to high throughput methods of determining a viral titer. The instant invention addresses the need for a more rapid and cost effective method of quantitating infectious viral particles in a sample.

4 Claims, 8 Drawing Sheets

CCID: cell culture infective dose (56) References Cited

OTHER PUBLICATIONS

Erika Hammarlund et al: "A Flow Cytometry-Based Assay for Quantifying Non-Plaque Forming Strains of Yellow Fever Virus", PLOS ONE, vol. 7, No. 9, Sep. 19, 2012 (Sep. 19, 2012), p. e41707, XP55524798, DOI: 10.1371 /journal.pone.0041707.

* cited by examiner

Figure 1

Sample of dilutions

STEPS

| | | | | | |
|---|---|---|---|---|---|
| Arithmetic dilution factor | 1/10 | 1/100 | 1/400 | 1/1600 | 1:6400 ......... |
| Dilution factor in $\log_{10}$ | 1.0 | 2.0 | 2.6 | 3.2 | 3.8............ |
| Micro-tubes: | | | | | |
| Volume of the dilution medium | 0.1+ 0.9 | 0.1+ 0.9 | 0.250+0.750 | 0.250+0.750 | 0.250+0.750 |

Figure 2

Example of plate design in a conventional plate assay

| Log dilution | | 1 | 2 | 3 | 4 | 5 | 6 | 7 | 8 | 9 | 10 | 11 | 12 |
|---|---|---|---|---|---|---|---|---|---|---|---|---|---|
| 2.6 | A | | | | | | | | | | | | |
| 3.2 | B | | | | | | | | | | | | |
| 3.8 | C | | | | | | | | | | | | |
| 4.4 | D | | | | | | | | | | | | |
| 5.0 | E | | | | | | | | | | | | |
| 5.6 | F | | | | | | | | | | | | |
| 6.2 | G | | | | | | | | | | | | |
| cell control | H | | | | | | | | | | | | |
| | | Virus control dilutions | | | | | | Virus tested | | | | | |

Figure 3

Sample of plate design in high throughput virus titration

Figure 4

Sample of plate design in high throughput virus titration

|   | 1 | 2 | 3 | 4 | 5 | 6 | 7 | 8 | 9 | 10 | 11 | 12 |
|---|---|---|---|---|---|---|---|---|---|---|---|---|
| A | Virus control | | Sample 1 | | Sample 2 | | Sample 3 | | Sample 4 | | Sample 5 | |
| B | | | | | | | | | | | | |
| C | | | | | | | | | | | | |
| D | | | | | | | | | | | | |
| E | | | Sample 6 | | Sample 7 | | Sample 8 | | Sample 9 | | validation control | |
| F | | | | | | | | | | | | |
| G | | | | | | | | | | | | |
| H | Cell control | | | | | | | | | | | |

Figure 5

Linear regression of CPV2

$y = 0.9271x - 0.8501$
$R^2 = 0.9653$

X-axis: Theoretical mean titer ($Log_{10}$ CCID50/mL)
Y-axis: Number of infected cells peer well (Log)

CCID: cell culture infective dose

Figure 6

Comparison between conventional virus titer method and high throughput virus titer method for CPV2

Figure 7

Linear regression of Pox virus (Avian ALVAC) expressing an equine influenza antigen y = 0,8278x + 1,6959
$R^2$ = 0,9567

Dilution Log

Figure 8

Comparison between conventional virus titer method and high throughput virus titer method for Pox virus (Avian ALVAC) expressing an equine influenza antigen — Titration - conventional
— Titration - CellInsight Samples

HIGH THROUGHPUT METHODS FOR VIRUS QUANTIFICATION

CROSS-REFERENCE TO RELATED APPLICATIONS

This application claims priority to U.S. provisional application 62/196,886 filed on Jul. 24, 2015.

FIELD OF THE INVENTION

This invention relates to high throughput methods of determining a viral titer. The instant invention addresses the need for a more rapid and cost effective method of quantitating infectious viral particles in a sample.

BACKGROUND OF THE INVENTION

A particular challenge in the delivery of a gene by a viral vector or a virus for therapeutic purposes is the preparation and accurate quantification of clinical dosage forms. The production of viral vaccines, recombinant proteins using viral vectors and viral antigens all require virus quantification to continually adapt and monitor the process in order to optimize production yields and respond to the ever changing demands and applications.

Virus titer determination or virus quantification involves counting the number of viruses in a specific volume to determine the virus concentration. Traditional methods include viral plaque assays which determine the number of plaque forming units (pfu) in a virus sample and the Tissue Culture Infective Dose ($TCID_{50}$) or Fluorescence Active Infectious Dose (FAID50) which measures the infectious virus titer. This $TCID_{50}$ assay quantifies the amount of virus required to kill 50% of infected hosts or to produce a cytopathic effect in 50% of inoculated tissue culture cells. The traditional methods are generally slow and labor-intensive, and suffer from limitations including a high degree of inter-assay variability.

Enzyme-Linked Immunosorbent Assay (ELISA) is a more modern variation of a protein assay that utilizes a specific antibody linked to an enzyme to detect the presence of an unknown amount of antigen (i.e. virus) in a sample. The antibody-antigen binding event is detected and/or quantified through the enzyme's ability to convert a reagent to a detectable signal that can be used to calculate the concentration of the antigen in the sample. The plate assays of the virus titer determination that are based on immunofluorescence detection using an ELISA are developed, however they are used to quantify proteins from virus samples and not to quantify infectious viruses.

Flow cytometry or FACS (fluorescence-activated cell sorter) assays have been used to measure the number of infected cells in cell cultures infected at relatively high multiplicities of infection. For example, U.S. Pat. No. 6,248,514 discloses the use of flow cytometry to analyze cells infected using specified ranges of viral particle concentration and adsorption time yields. U.S. Pat. No. 7,476,507 discloses FACS-based methods for the determination of the viral titer of a culture of host animal host cells infected with a circovirus. However, for many applications, the cost, size and complexity of the flow cytometry instruments prevent wider use.

Recently, personal image cytometers are developed which combine the functions of a digital microscope, an image cytometer, and a cell counter in a single benchtop instrument. The commercially available image cytometers include CellInsight (ThermoFisher) and Cytell Cell Imaging System (GE Healthcare). These image cytometers are used to make individual cell, subcellular and multi-cellular measurements, and provide the opportunity for scientists to capture cellular and subcellular image data and analyze results with ease.

The instant invention addresses the need for an accurate and high throughput method of quantitating infectious viral particles in a sample.

SUMMARY OF THE INVENTION

This invention provides high throughput methods for the rapid determination and quantification of the infectious virus produced in a sample. The invention also provides high throughput methods for the rapid determination and quantification of the infectious virus produced in a batch culture such that an optimum harvesting point can be obtained. The methods encompass providing a sample containing a virus, preparing serial dilutions of the sample, infecting host cells therewith and incubating the culture at an appropriate temperature, reacting an antigen expressed by the virus in infected cells with an antibody labeled with a fluorescent tag, determining the number of fluorescence tagged cells, thereby determining the virus titer in the sample. The high throughput methods may be carried out in a multiple-well plate format. In one embodiment, CellInsight (ThermoFisher) is used.

In one aspect of the embodiment, a straight line is plotted using linear regression between number of fluorescence cells and virus titer using a virus reference.

In another aspect of the embodiment, at least one of the serial dilutions of the sample falls within the range of the liner regression line.

In yet another aspect of the embodiment, the multi-well plates are used.

In yet another aspect of the embodiment, the number of infected cells in each well is determined by an image cytometer, such as CellInsight.

The virus can be wild-type virus, attenuated virus, or recombinant virus. When the virus is a recombinant virus, the antigen can be encoded by an exogenous gene. Typically the antigen reacts with at least one antibody, although the antibody can be a mixture of antibodies. The antibody can be polyclonal or monoclonal.

The sample can be a sample collected from fields, sample from optimization process, seed sample, main culture sample, active ingredient, or final product.

These and other embodiments are disclosed or are obvious from and encompassed by, the following Detailed Description.

BRIEF DESCRIPTION OF DRAWINGS

The following detailed description, given by way of examples, but not intended to limit the invention solely to the specific embodiments described, may best be understood in conjunction with the accompanying drawings, incorporated herein by reference, in which.

The seed cultures developed as a result of the use of the methods of the invention can be used to seed large volume fresh cell culture medium, in the order of 5-1000 liter volumes or more. In this procedure, the seed culture harvested is inoculated into a large-scale culture comprising cell culture medium.

This invention, therefore, provides a high throughput procedure for the in-process monitoring and rapid determination of the useful harvesting point of a cell culture infected with a virus such that an optimum yield of the virus can be obtained. The methods encompass providing a seed culture of a virus infected host cells and inoculating a batch culture therewith, incubating the culture, removing samples of the cultured cells, preparing serial dilutions of the samples, reacting an antigen expressed by the virus in infected cells with an antibody labeled with a fluorescent tag, determining the number of fluorescence cells, thereby determining the virus titer in the batch culture. It is contemplated that the methods of the invention can be usefully applied for detecting and in-process monitoring of the production of any virus cultured on isolated host cells and for which there are available viral antigen specific antibodies.

In the various embodiments of this method of the invention, the viruses can be any viruses, including DNA viruses, RNA viruses, recombinant viruses, viruses carrying transgenes, baculoviruses expressing antigens, etc. The viruses may include, but are not limited to, adenovirus, retrovirus, herpes simplex virus, parvovirus, classical swine fever virus, influenza virus, circovirus (including porcine circovirus PCV1 and PCV2), porcine reproductive and respiratory syndrome virus, rotavirus, bovine viral diarrhea virus, porcine epidemic diarrhea virus, sindbis virus, baculovirus, pseudorabies virus, varicella-zoster virus, cytomegalovirus, vesicular stomatitis virus, hepatitis A, B, and C viruses, pox virus, foot-and-mouth disease virus, bluetongue virus, newcastle disease virus, infectious bursal disease virus, Marek's disease virus, infectious laryngotracheitis virus, avian paramyxovirus, westnile virus, nipah virus, hendra virus, African horse sickness virus, canine distemper virus, leukemia virus, calicivirus, Schmallenberg virus, and recombinant viruses thereof.

It should be understood that the present invention is not limited to the specific compositions, equipment or methods described herein and that any composition having formula or method steps equivalent to those described falls within the scope of the present invention. It will also be understood that although the form of the invention shown and described herein constitutes preferred embodiments of the invention, it is not intended to illustrate all possible forms of the invention. The words used are words of description rather than of limitation. Various changes and variations may be made to the present invention without departing from the spirit and scope of the invention.

The invention is further described by the following non-limiting examples:

EXAMPLES

Example 1 Summary of the Current Virus Titration Plate Assay

The viruses used in this example were canine parvovirus (CPV) and recombinant pox virus (avian canarypox virus) expressing an equine influenza antigen. The host cell line is canine myeloma cells A72.

Host Cells Preparation

A fresh suspension of host cells was prepared in DMEM medium+5% FCS (Fetal Calf Sera) at a concentration of 60 000 cells/ml. 150 µl of this cell suspension was added into each well of a 96-well plate.

Sample Dilutions

Figure 1:
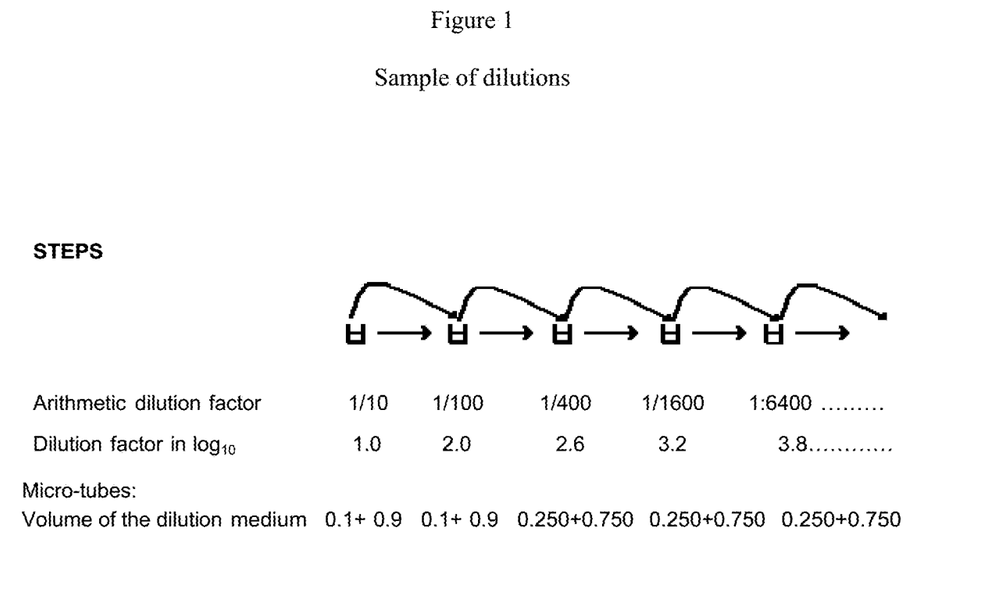
FIG. 1 illustrates a sample of dilutions.

An aliquot was taken from a sample containing a virus and serial dilutions were carried out in micro tubes according to, for example, the table shown in FIG. 1. The virus control (virus reference) was diluted following the same procedure.

Plate Design

Figure 2:
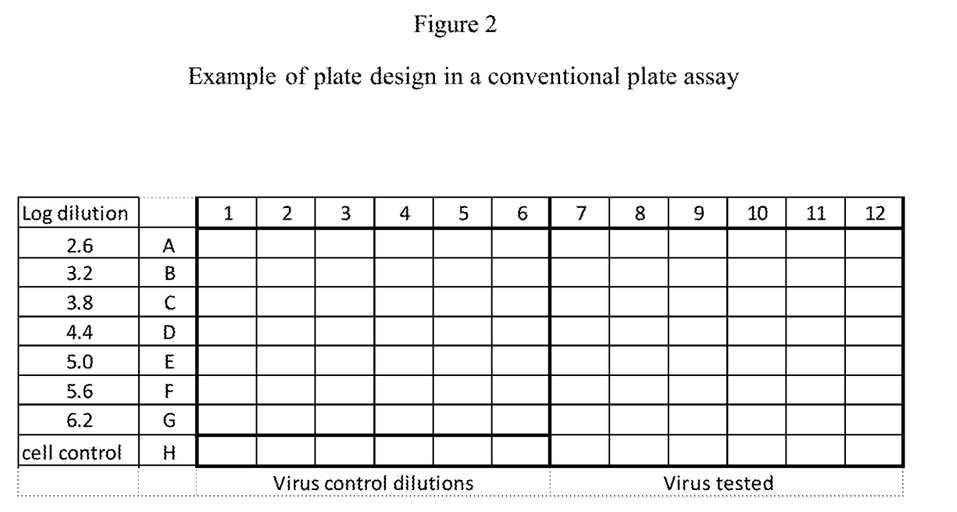
FIG. 2 illustrates a sample of plate design in a conventional plate assay.

The prepared dilutions that encompass the expected titer were dispensed into the plate as shown in FIG. 2. To each well containing 150 µl of the cell suspension, 100 µl of the diluted samples were added. For cell controls (line H) (at least one cell control per session), 100 µl of dilution medium was added to the cell suspension. The number of sample dilutions was 8. The number of virus control dilutions was 7. The number of wells per dilution is 6. In this plate design, for one plate, total of 42 wells were used for virus control (virus reference), 6 wells were used for cell control, and 48 wells were used to assay one sample. In some cases, 144 wells (one and a half 96-well plates) were used to read one sample, and the resulting three results per sample were used to calculate the average reading of the sample.

In this method, to calculate a titer of a sample, one or two 96-well plates are needed to obtain an accurate titer determination.

Virus Infection of Host Cells in 96-Well Plates

The plates were incubated for 4 days in an incubator at around 37° C. with 5% $CO_2$. At the end of the incubation period, the control wells had to be checked under an inverted microscope for the completion of the cell layer without toxicity and pollution.

Fixation of Plates for Immunofluorescence Reaction

The plates were fixed with acetone. Briefly, the plates were washed once with $PBS^{2-}$ Buffer Saline Phosphate without calcium and magnesium. 100 µl/well of cold acetone 90% (10% of water) was added to the plates and the plates were incubated at −20° C. for 30 min. The acetone was discarded and the plates were completely air-dried.

Immunofluorescence Reaction

For the immunofluorescence reaction, 100 µl/well monoclonal antibody (anti-CPV2 for CPV or anti-EIV antigen for the recombinant Canarypox-equine influenza antigen) was added to the plates and the plates were incubated at 37° C. for 30 min. The plates then were washed twice using PBS. 100 µl/well anti-mouse FITC was added to the plates and the plates were incubated at 37° C. for 30 min. The plates were washed with PBS twice and followed by a rapid wash in neutral water.

Titer Calculation

The plates were read by UV light with filter 488-519λ. For identification, the well is positive if one or more cells are fluorescent.

The calculation of the titer is carried out by angular transformation or according to Karber's method, for which the formula is:

$$T=d+[r/N]\times[n+N/2]+1$$

T=titer
d=dilution with 100% of wells to show a fluorescent focus
r=dilution ratio
N=number of wells per rate dilution
n=number of wells showing a fluorescence for rate dilution above d Example 2 Improved High Throughput Method of Virus Titration The viruses used in this example were canine parvovirus (CPV) and recombinant pox virus (avian canarypox virus) expressing an equine influenza antigen. The host cell line is canine myeloma cells A72.

Host cells preparation was carried out as described in Example 1.

Sample Dilution

Sample dilution was carried out as described in Example 1.

Plate Design

Figure 3:
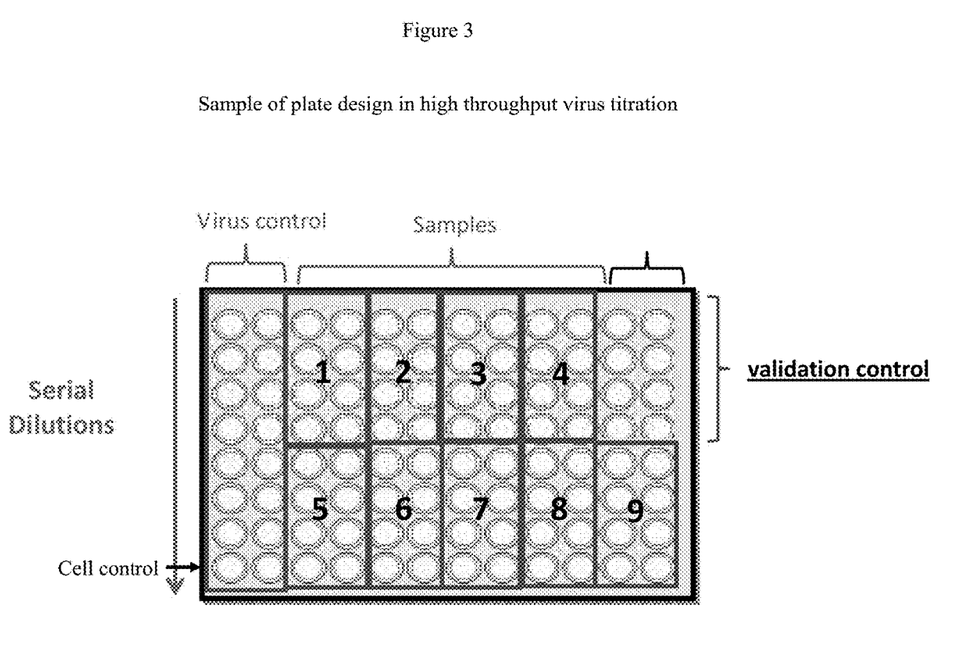
FIG. 3 illustrates a sample of plate design in high throughput virus titration.
Figure 4:
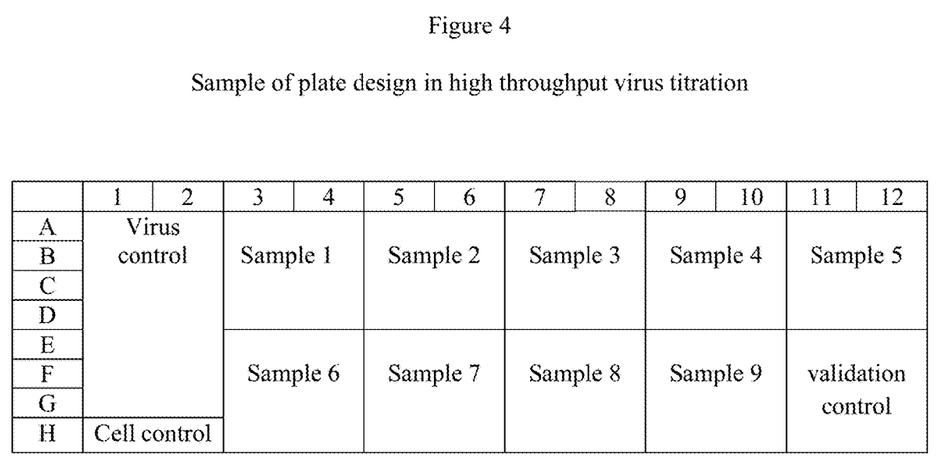
FIG. 4 illustrates a sample of plate design in high throughput virus titration.

A sample plate is shown in FIGS. 3 and 4. In these plate designs, the number of sample dilutions was 4. The number of virus control dilutions was 7. The number of wells per dilution is 2. For one plate, total of 14 wells were used for virus control (virus reference), 2 wells were used for cell control, 8 wells were used for validation control per session (each session may contain multiple plates), and 8 wells were used to assay one sample for a total of 9 samples. Virus reference was used to plot the linear regression line and to calculate the titer of the unknown sample. Cells control were wells without any virus to check that the session worked well. Validation control contains a virus (other than the virus reference) with known titer. Validation control was titrated on each plate and its titer was calculated and the results were included in the chart control. Validation control provides quality control of the session and ensures that the session worked well.

Virus infection of host cells in 96-well plates, Fixation of plates for immunofluorescence reaction, and Immunofluorescence reaction were carried out as described in Example 1.

Titer Calculation

Figure 5:
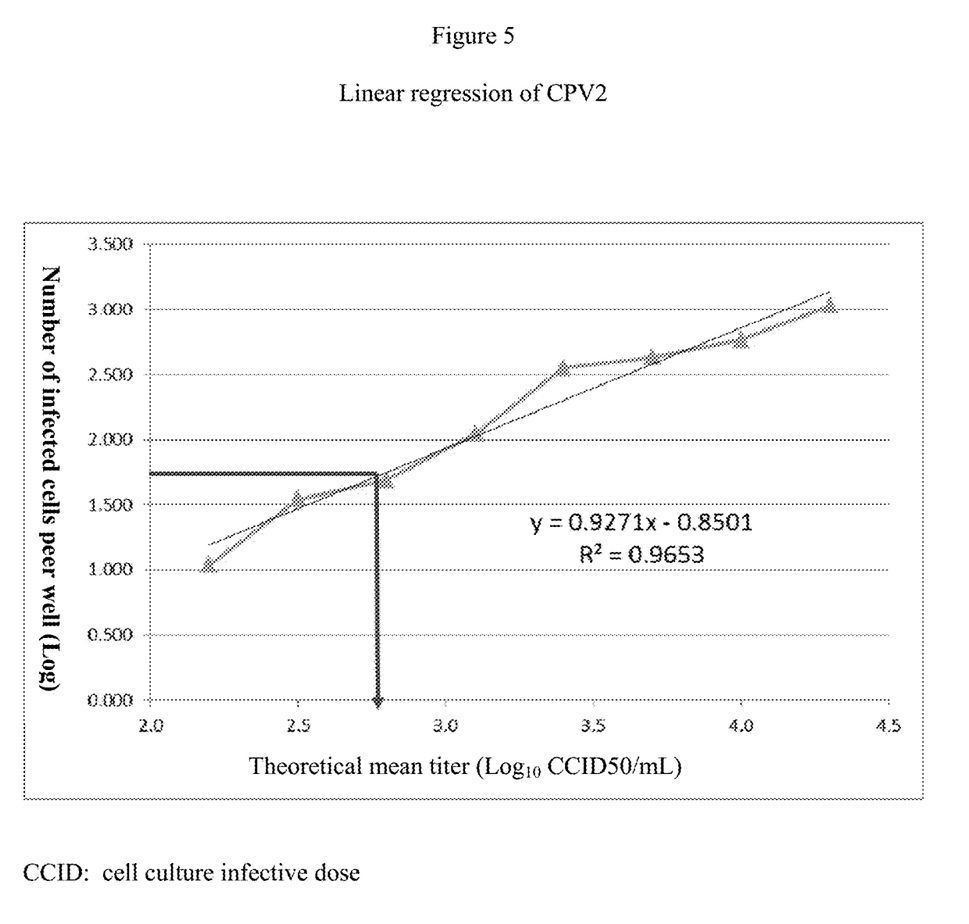
FIG. 5 depicts the linear regression of CPV2.
Figure 7:
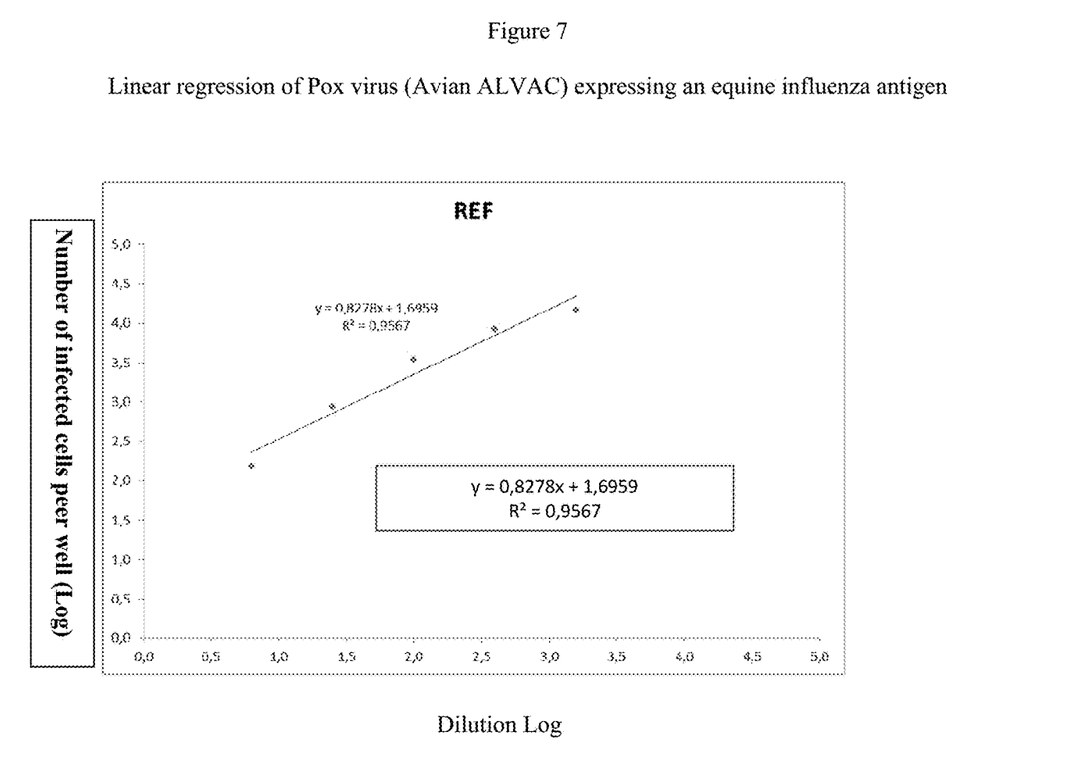
FIG. 7 depicts the linear regression of Pox virus (Avian ALVAC

The number of infected cells per well was read using CellInsight. A straight line is plotted using linear regression between number of fluorescence cells per well and virus titer using the virus control (virus reference) as shown in FIG. 5 (CPV) and FIG. 7 (recombinant pox virus). The virus titer of a sample is then calculated using the straight line (linear regression of reference virus) based on the reading of the infected cells per well of that sample and its dilution factor.

Results

Figure 6:
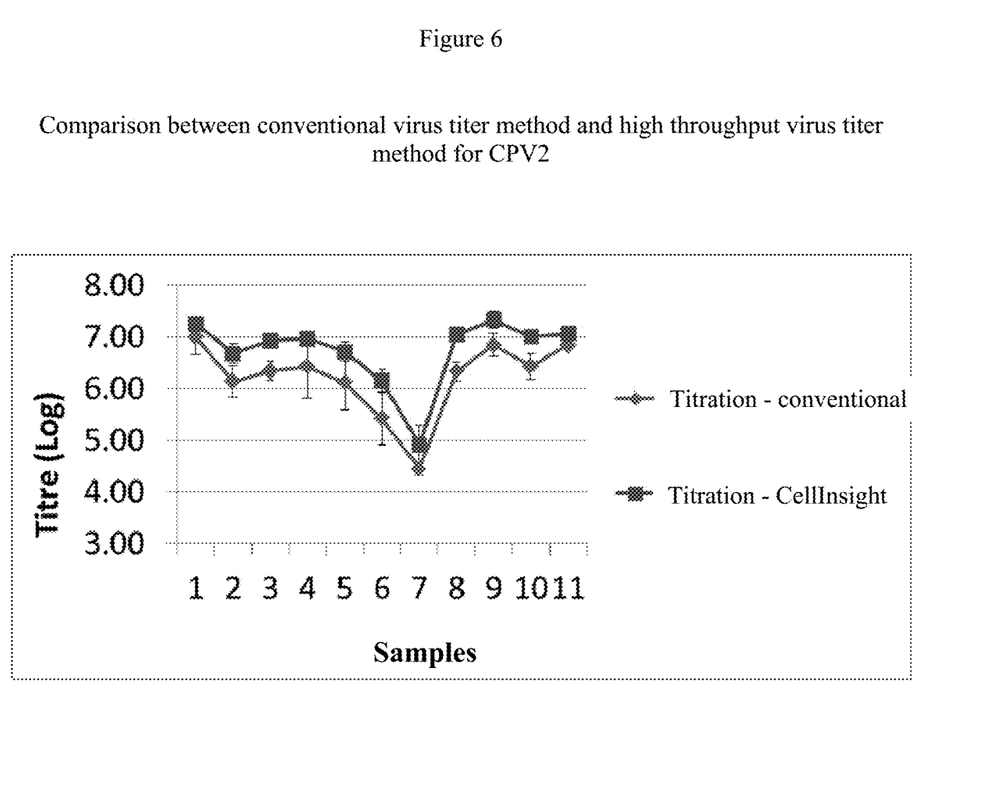
FIG. 6 depicts the comparison between conventional virus titer method and high throughput virus titer method for CPV2.
Figure 8:
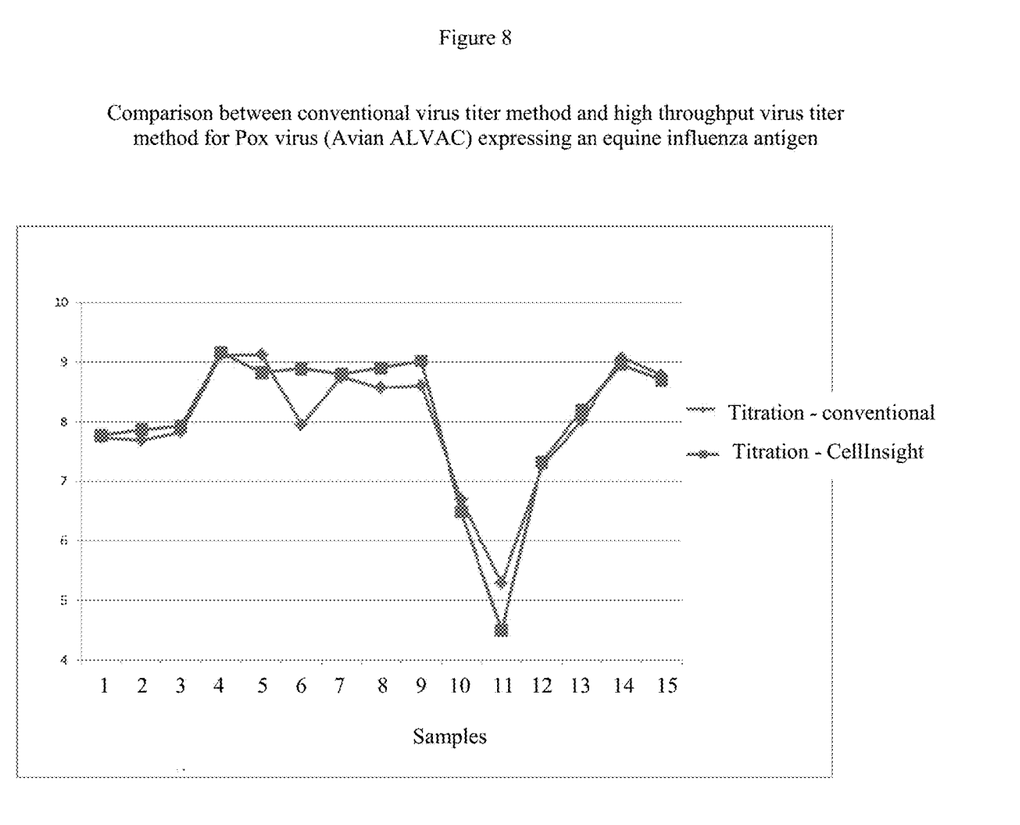

The virus titer calculated using the improved method was compared to the virus titer calculated using the conventional method. FIG. 6 shows the results for CPV. FIG. 8 shows the results for recombinant pox virus. The results demonstrated that the high throughput method which determines the infected cells collates well with the conventional virus titer determination method (conventional plate assay) which counts the wells containing infected cells (fluorescence tagged cells).

Discussion

This high throughput method provides the advantage of reducing the number of dilutions and duplicates that is necessary to accurately calculate the virus titer, and therefore the increase of number of samples to be titrated on one plate.

Having thus described in detail preferred embodiments of the present invention, it is to be understood that the invention defined by the appended claims is not to be limited by particular details set forth in the above description as many apparent variations thereof are possible without departing from the spirit or scope thereof.

All documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention

What is claimed is:

1. A method of virus titer determination comprising:
   1) providing a sample containing a virus selected from a parvovirus or a recombinant pox virus of the Poxviridae virus family;
   2) preparing serial dilutions of the sample;
   3) infecting host cells contained in the serial dilutions with the virus and incubating the host cells;
   4) reacting an antigen expressed by the virus in the infected host cells with an antibody labeled with a fluorescent tag;
   5) determining the number of infected host cells in each serial dilution by reading the fluorescent tags by using an image cytometer;
   6) comparing the determined number of infected host cells in each serial dilution to a reference curve, wherein the reference curve is a straight line plotted using linear regression between number of infected cells and the corresponding virus titer using serial dilutions of a virus reference with a known virus titer;
   7) determining a reference virus titer corresponding to the determined number of infected host cells in each serial dilution; and
   8) calculating the virus titer in the sample using the dilution factor of each serial dilution and the determined reference virus titer.

2. The method of claim 1, wherein the method is carried out in a multi-well plate.

3. The method of claim 1, wherein the fluorescence fluorescent tag is selected from FITC, Hoechst stain, DAPI, GFP, TRITC, and Cy5.

4. The method of claim 1, wherein the number of infected host cells of at least one of the serial dilutions falls within a range defined by the linear portion of the linear regression line of the reference virus.

* * * * *